United States Patent [19]

Varasi et al.

[11] Patent Number: 5,449,692

[45] Date of Patent: * Sep. 12, 1995

[54] SUBSTITUTED (ARYLALKYLAMINOBENZYL) AMINOPROPIONAMIDE DERIVATIVES AND PROCESS FOR THEIR PREPARATION

[75] Inventors: Mario Varasi, Milan, Italy; Philippe Dostert, Paris, France; Paolo Pevarello, Pavia; Alberto Bonsignori, Milan, both of Italy

[73] Assignee: Farmitalia Carlo Erba S.r.l., Milan, Italy

[*] Notice: The portion of the term of this patent subsequent to Aug. 17, 2010 has been disclaimed.

[21] Appl. No.: 215,694

[22] Filed: Mar. 22, 1994

[30] Foreign Application Priority Data

Apr. 1, 1993 [GB] United Kingdom ............... 9306899

[51] Int. Cl.⁶ ................. A61K 31/165; C07C 233/05
[52] U.S. Cl. ........................... 514/620; 514/617; 514/618; 514/619; 564/162; 564/163; 564/164; 564/165; 564/167; 564/168; 564/171
[58] Field of Search .............. 564/163, 167, 164; 514/619, 620

[56] References Cited

U.S. PATENT DOCUMENTS

| | | |
|---|---|---|
| 4,049,663 | 9/1977 | Harper et al. |
| 4,513,009 | 4/1985 | Roques et al. |
| 4,631,287 | 12/1986 | Chakraborty et al. |
| 4,639,468 | 1/1987 | Roncucci et al. |
| 4,725,619 | 2/1988 | Chakraborty et al. |
| 4,728,668 | 3/1988 | Chakraborty et al. |
| 4,839,369 | 6/1989 | Youssefyeh et al. |
| 5,236,957 | 8/1993 | Dostert et al. |

FOREIGN PATENT DOCUMENTS

0400495 12/1990 European Pat. Off. .
1140748 1/1969 United Kingdom .

OTHER PUBLICATIONS

Eur. Neuropsychopharmacol. 1/ 317–319, 1991, P. Dostert, et al., "New Anticonvulsants with Selective Mao-B Inhibitory Activity".

Primary Examiner—Shailendra Kumar
Attorney, Agent, or Firm—Oblon, Spivak, McClelland, Maier & Neustadt

[57] ABSTRACT

The invention provides new compounds of formula (I)

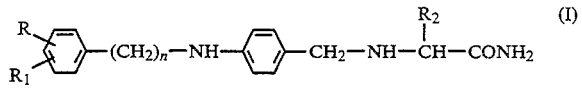

wherein n is an integer of 1 to 4; each of R and $R_1$, which may be the same or different, is hydrogen, halogen, trifluoromethyl or $C_1$–$C_4$ alkoxy; R2 is hydrogen or $C_1$–$C_4$ alkyl; and a pharmaceutically acceptable salts thereof; and wherein when, at the same time, R is hydrogen, $R_1$ is hydrogen or halogen and n is one, then $R_2$ is other than hydrogen or methyl; and of formula (IA)

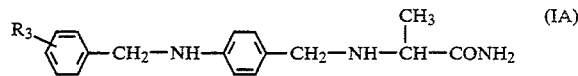

wherein $R_3$ is halogen, and a pharmaceutical acceptable salt thereof, which are active on the central nervous system (CNS) and can be used in therapy as anti-epileptics, anti-Parkinson, neuroprotective, antidepressant, anti-spastic and hypnotic agents.

7 Claims, No Drawings

SUBSTITUTED (ARYLALKYLAMINOBENZYL) AMINOPROPIONAMIDE DERIVATIVES AND PROCESS FOR THEIR PREPARATION

The present invention relates to substituted (phenylalkylaminobenzyl)aminopropanamide derivatives, to their use as therapeutic agents, to a process for their preparation and to pharmaceutical compositions containing them. Other N-substituted α-amino carboxamide derivatives are known as having pharmacological properties, for instance those described by British patent No. 1140748. The compounds according to this prior art document are useful in the treatment and prophylaxis of such diseases as coronary artery disease and atherosclerosis; moreover they are useful in the treatment of inflammatory conditions such as rheumatoid arthritis.

Further substituted amino acid derivatives are known as enkephalinase inhibitors, analgesics and hypotensives from EP-A-0038758.

Still other substituted glycine and alanine derivatives are disclosed by U.S. Pat. No. 4,049,663. The compounds according to this document have utility as oral analgesics. International patent application WO-90/14334 discloses N-phenylalkyl substituted α-amino carboxamide derivatives active on the central nervous system.

It has now been found that new substituted (arylalkylaminobenzyl)aminopropanamide derivatives, which are a selected class of those disclosed in WO-90/14334 by the present applicants, have valuable biological properties, in particular as anti-epileptic, anti-Parkinson, neuroprotective, antidepressant, antispastic, and/or hypnotic agents.

Accordingly the present invention provides a new compound of formula (I)

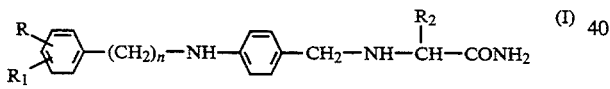

wherein n is an integer of 1 to 4; each of R and R=, which may be the same or different, is hydrogen, halogen, trifluoromethyl or $C_1$-$C_4$ alkoxy; $R_2$ is hydrogen or $C_1$-$C_4$ alkyl; or a pharmaceutically acceptable salt thereof; and wherein when, at the same time, R is hydrogen, $R_1$ is hydrogen or halogen and n is one, then $R_2$ is other than hydrogen or methyl. A halogen atom is preferably fluorine, chlorine or bromine, in particular fluorine or chlorine.

A —$(CH_2)_n$—group may be a branched or straight alkylene chain.

A $C_1$-$C_4$ alkoxy group may be a branched or straight group, typically methoxy, ethoxy, propoxy, isopropoxy, butoxy or tert-butoxy, preferably methoxy or ethoxy.

A $C_1$-$C_4$ alkyl group may be a branched or straight group, typically methyl, ethyl, propyl, isopropyl, butyl or tert-butyl, preferably methyl or ethyl.

Preferred compounds of the invention are the compounds of formula (I) wherein, subject to the above proviso, n is 1, 2, 3 or 4;

R is hydrogen; $R_1$ is hydrogen, halogen, $C_1$-$C_4$ alkoxy or trifluoromethyl;

$R_2$ is $C_1$-$C_4$ alkyl; and the pharmaceutically acceptable salts thereof.

Specific examples of preferred compounds or the invention are:

2-[4-(2-methoxybenzyl)aminobenzyl]aminopropanamide;
2-[4-(3-methoxybenzyl)aminobenzyl]aminopropanamide;
2-[4-(2-trifluoromethylbenzyl)aminobenzyl]aminopropanamide;
2-[4-(3-trifluoromethylbenzyl)aminobenzyl]aminopropanaimide;
2-{4-[2-(2-fluorophenyl)ethyl]aminobenzyl}aminopropanamide;
2-{4-[2-(3-fluorophenyl)ethyl]aminobenzyl}aminopropanamide;
2-{4-[3-(2-fluorophenyl)propyl]aminobenzyl}aminopropanamide;
2-{4-[3-(3-fluorophenyl)propyl]aminobenzyl}aminopropanamide;
2-{4-[4-(3-fluorophenyl)butyl]aminobenzyl}aminopropanamide;
2-[4-(3-phenylpropyl)aminobenzyl]aminopropanamide;
2-[4-(2-phenylethyl)aminobenzyl]aminopropanamide;
2-{4-[4-(2-fluorophenyl)butyl]aminobenzyl}aminopropanamide;
2-[4-(4-phenylbutyl)aminobenzyl]aminopropanamide;

if the case, either as single (S) or (R) isomer or as a mixture thereof and the pharmaceutically acceptable salts thereof.

The present invention also provides a new compound of formula (IA)

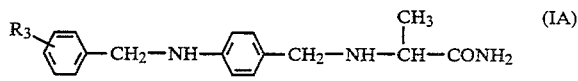

wherein $R_3$ is halogen; or a pharmaceutically acceptable salt thereof.

Compounds of formula (IA) are a further selected class of compounds according to WO-90/14334.

Specific examples of preferred compounds of formula (IA) are the following:

2-[4-(4-fluorobenzyl)aminobenzyl]aminopropanamide;
2-[4-(4-chlorobenzyl)aminobenzyl]aminopropanamide;
2-[4-(4-bromobenzyl)aminobenzyl]aminopropanamide;
2-[4-(3-fluorobenzyl)aminobenzyl]aminoproppnamide;
2-[4-(3-chlorobenzyl)aminobenzyl]aminopropanamide;
2-[4-(2-bromobenzyl)sminobenzyl]aminopropanamide;
2-[4-(2-chlorobenzyl)aminobenzyl]aminopropanamide;
2-[4-(2-fluorobenzyl)aminobenzyl]aminopropanamide;
2-[4-(3-bromobenzyl)aminobenzyl]aminopropanamide; if the case, either as single (S) or (R) isomer or as a mixture thereof, and the pharmaceutically acceptable salts thereof.

The compounds of formula (I) and (IA) and their salts are hereafter referred to as the "active compounds" and as the "compounds of the invention".

The present invention includes all the possible optical isomers of the compounds of formulae (I) and (IA) and their mixtures, as well as the metabolites thereof.

The present Invention also includes within its scope pharmaceutically acceptable bioprecursors and prodrugs of the compounds of formulae (I) and (IA) i.e. compounds, which have a formula different to formula (I) and (IA), respectively, but which nevertheless are directly or indirectly converted in vivo into a compound of formula (I) or (IA), respectively, upon administration to a human being.

Pharmaceutically acceptable salts of the compounds of formulae (I) and (IA) include acid addition salts with inorganic acids, e.g. nitric, hydrochloric, hydrobromic, sulphuric, parabiotic, and phosphoric acid, or organic acids, e.g. acetic, propionic, glycolic, lactic, oxalic, malonic, malic, tartaric, citric, benzoic, cinnamic, mandelic, methanesulfonic and salicylic acids.

The compounds of formula (I) and the pharmaceutically acceptable salts thereof can be obtained by a process comprising a) reacting a compound of formula (II)

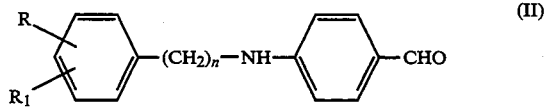

wherein

R, $R_1$ and n are as defined above, with a compound of formula (III)

wherein $R_2$ is as defined above; or b) reacting a compound of formula (IV) or a reactive derivative thereof

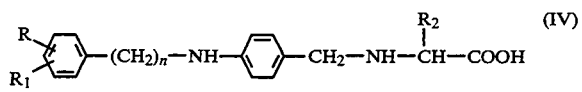

wherein

R, $R_1$, $R_2$ and n are as defined above, with ammonia; or c) reacting a compound of formula (V)

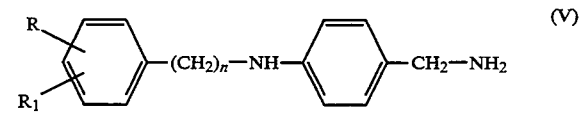

wherein

R, $R_1$ and n are as defined above; with a compound of formula (VI)

wherein

W is a halogen atom and $R_2$ as defined above; and, if desired converting a compound of formula (I) into another compound of formula (I), and/or, if desired, converting a compound of the invention into a pharmaceutically acceptable salt and/or, if desired, converting a salt into a free compound and/or, if desired, separating a mixture of isomers of compounds of the invention into the single isomers.

All the processes described hereabove are analogy processes and can be carried out according to well known methods in organic chemistry.

The reaction of a compound of formula (II) with a compound of formula (III) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C., to about 40° C., in the presence of a reducing agent, the most appropriate being sodium cyanoborohydride. Occasionally molecular sieves can be added to the reaction mixture for facilitating the reaction.

A reactive derivative of a compound of formula (IV) may be for instance an alkyl ester thereof e.g. a $C_1$–$C_6$ alkyl ester such as a $C_1$–$C_4$ alkyl ester and, in particular a methyl, ethyl or propyl ester, which may be unsubstituted or substituted by a phenyl ring optionally substituted by a nitro group.

Preferably an alkyl ester of a compound of formula (IV) is used.

The reaction of a compound of general formula (IV) or a reactive derivative thereof, with ammonia can be performed using an excess of ammonia, optionally in the presence of water or of an organic solvent, such as dimethylformamide. The temperature of the reaction may range from about 20° C. to about 100° C.

In a a compound of formula (VI) W is preferably bromine or chlorine. The reaction of a compound of general formula (V) with a compound of general formula (VI) can be carried out in a suitable organic solvent, such as an alcohol, e.g. ethanol, or in dimethylformamide, at a temperature ranging from about 40° C. to about 140° C. in the presence of a suitable acid acceptor e.g. anhydrous potassium carbonate.

A compound of the invention can be converted, as stated above, into another compound of the invention by known methods.

Also the optional salification of a compound of the invention as well as the conversion of a salt into the free compound and the separation of a mixture of isomers into the single isomers may be carried out by conventional methods.

The compounds of formulae (II) to (VI) are either known compounds or may be obtained according to known methods, e.g. as described in W90-90/14334, and in the Examples which follow.

The compounds of formula (IA) and the pharmaceutically acceptable salts thereof can be obtained by any one of process variants a) to c) described above for the preparation of compounds of formula (I).

The compounds of formula (IA) and the pharmaceutically acceptable salts thereof are preferably obtained by a process comprising reacting a compound of formula (VII)

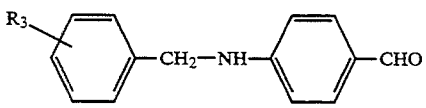

wherein $R_3$ is as defined above, with a compound of formula (VIII)

and, if desired converting a compound of formula (IA) into another compound of formula (IA), and/or, if desired converting a compound of formula (IA) into a pharmaceutically acceptable salt and/or, if desired, converting a salt into a free compound, and/or, if desired, separating a mixture of isomers of of formula (IA) into the single isomers.

The reaction of a compound of formula (VII) with a compound of formula (VIII) can be carried out by following the same reaction conditions described above in connection with the reaction of a compound of formula (II) with a compound of formula (III).

Also the additional optional steps described above, as well as the salification of a compound of formula (IA), can be performed according to known methods.

The compounds of formula (VII) and (VIII) on either known or can be obtained by known methods.

When in the compounds of the present invention and in the intermediate-products thereof, groups are present, which need to be protected before submitting them to the hereabove illustrated reactions, they may be protected before being reacted and then deprotected, according to methods well known in organic chemistry.

The intermediate compounds, according to the processes herein described for the preparation of the compounds of the invention, may be either in the form of a single isomer or as a mixture thereof. Preferably they are in the form of a single isomer.

PHARMACOLOGY

The compounds of he invention are active on the central nervous system (CNS) and can be used in therapy, for example, as anti-epileptics, in the treatment of Parkinson's disease and as neuroprotective agents in degenerative processes associated with normal ageing or pathological situations, such as brain ischemia; they can also be used as antidepressants, hypnotics and anti-spastic agents.

The activity on the CNS of the compounds of the invention was evaluated on the basis of pharmacological methods, such as, for example, the antagonism of convulsions and lethality induced by intravenous injection of bicuculline in mice (Antiepileptic Drugs, D. M. Woodbury et al. eds., 2nd edition, Raven Press, New York, 1982), or the antagonism of maximal electroshock seizures (MES) (Woodbury, L.A. and Davenport V.D., Arch. Int. Pharmacodyn. Ther. 92; 97–104, 1952).

The neurotoxicity of the compounds and of the reference anticonvulsants was assessed with the rotorod test (Dunan and Miye, J. Am. Pharm. Ass. Sci. Ed., 1957, 46, 208; Kinnard et al. J. Pharmacol. Exp. Ther. 1957, 121, 354; Horowitz, Nature, 1963, 200, 369).

For instance, following Table 1 summarizes the activity and neurotoxicity data obtained in the MES test and in the rotorod test, respectively, for a representative group of compounds according to the present invention, in comparison with the prior art compound 2-(4-benzyl-aminobenzyl)aminopropanamide, dihydrochloride (internal code FCE 26749) which is known from WO-90/14334.

TABLE 1

| Internal code FCE | MES - $ED_{50}$ (mg/kg) | ROTOROD-$TD_{50}$ (mg/kg) | TI |
| --- | --- | --- | --- |
| 28622 | 18.7 | 1642 | 88 |
| 28623 | 17.1 | 917 | 54 |
| 28639 | 29.1 | 1902 | 65 |
| 28640 | 26.5 | 1676 | 63 |
| 28714 | 11.3 | 663 | 59 |
| 27232 | 6.4 | 516 | 81 |
| 26749 | 9.5 | 217 | 23 | wherein:
$ED_{50}$ means effective dose in 50% of treated animals
$TD_{50}$ means toxic dose in 50% of treated animals
TI means therapeutic index ($TD_{50}/ED_{50}$)
FCE 28622 means 2-[4-(4-chlorobenzyl)aminobenzyl]aminopropanamide, dihydrochloride;
FCE28623means2-[4-(2-phenylethyl)aminobenzyl]aminopropanamide, dihydrochloride;
FCE28639means2-[4-(4-bromobenzyl)aminobenzyl]aminopropanamide, dihydrochloride;
FCE 28640 means 2-[4-(4-fluorobenzyl)aminobenzyl]aminopropanamide, dihydrochloride;
FCE 28714 means 2-[4-(3-chlorobenzyl)aminobenzyl]aminopropanamide, dihydrochloride;
FCE 27232 means 2-[4-(3-fluorobenzyl)aminobenzyl]aminopropanamide, dihydrochloride.

From the comparative test data it is evident that the compounds of the present invention are endowed with a better therapeutic index than the prior art compound.

A patient is treated according to the present invention by a method comprising administering to the patient an effective amount of one of the compounds of the invention.

In this way the present compounds can be used to treat disorders of the central nervous system, for example epilepsy or Parkinson's disease, or as neuroprotective agents, anti-depressants, hypnotics or anti-spastic agents.

The condition of a patient may thus be improved.

The compounds of the invention can be administered in a variety of dosage forms. e.g. orally, in the form of tablets. capsules, sugar or film coated tablets, liquid solutions; rectally, in the form of suppositories; parenterally, e.g. intramuscularly or by intravenous injection or infusion.

The therapeutic regimen for the different clinical syndromes must be adapted to the type of pathology taking into account as usual, also the route of administration, the form in which the compound is administered and the age, weight and conditions of the subject involved. The oral route is employed, in general, for all conditions requiring such compounds. In emergency situations preference is given to intravenous injection.

For these purposes the compounds of the invention can be administered orally at doses ranging e.g. from about 20 to about 1500 mg/day. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum arabic, tragacanth, polyvlnylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention.

EXAMPLE 1 a) Methyl 4-(3-fluorobenzyl)aminobenzoate (1) 41 g (0.219 mol) of methyl 4-aminobenzoate hydrochloride are suspended in 500 ml of dry methanol and 10 g (0.159 mol) of sodium cyanoborohydride are added, while stirring under nitrogen. After ten minutes, 34.3 g (0.199 mol) of 3-fluorobenzaldehyde are added in a single portion. The reaction mixture is stirred seven hours at room temperature and then allowed to stand 16 hours. The solution is filtered and evaporated, taken up with water and extracted three times with methylene chloride. After drying and evaporating, the crude residue is chromatographed on silica gel (eluant: cyclohexane/ethyl acetate 4/1) to give methyl 4-(3-fluorobenzyl)aminobenzoate (27 g; 52%; m.p. 107°–110° C.).

b) Methyl 4-[N-t-butyloxycarbonyl-N-(3-fluorobenzyl)] aminobenzoate (2)

(1), (16 g; 0.0617 real) is dissolved in dichloromethane (350 ml) and treated with 4-dimethylaminopyridine (10.8 g; 0.0617 mol), di-t-butyldicarbonate (26.9 g; 0.123 mol) and triethylamine (12.4 ml) at room temperature for three hours. After evaporation and purification of the residue on silica gel (eluant: cyclohexane/ethyl acetate 7/3), 19 g (86%) of (2) are obtained, as a colorless oil. C) 4-[N-t-butyloxycarbonyl-N-(3-fluorobenzyl)]-aminobenzyl-alcohol(3)

The N-BOC-aminoester (2), (19 g; 0.0528 mol) is dissolved in 500 ml of ethyl ether under nitrogen and kept to $-70°$ C., while stirring. To this solution, a 1.2 M solution of diisobutyl aluminumhydride (DIBAH) (110 ml; 0.132 mol) is dropped slowly while temperature is maintained between $-70°$ and $-60°$ C. After 30' minutes at $-70°$ C., ethyl acetate (31 ml) is dropped and temperature allowed to raise to $-20°$ C.; then, water (15 ml) is cautiously added and the resulting mixture kept to room temperature for 1 hour. After filtration and washing of the residue with ethyl acetate, extraction and drying over sodium sulfate and evaporation, (3) (16.1 g; 92%) is obtained as an oil.

d) 4-[N-t-butyloxycarbonyl-N-(3-fluorobenzyl)-]aminobenzaldehyde (4)

To a mixture of DMSO (8.2 ml; 0.116 mol) in 250 ml of dichloromethane, 10.2 ml (0.0724 mol) of trifluoroacetic anhydride in 50 ml of dichloromethane are added, under nitrogen and stirring at $-70°$ C. After 15 minutes, a solution of 4-[N-t-butyloxycarbonyl-N-(3-fluorobenzyl)] aminobenzylalcohol in 100 ml of dichloromethane is dropped within an hour. After 30 minutes at $-70°$ C., the temperature is raised to $-20°$ C. and 65 ml of triethylamine are added while stirring. The mixture is allowed to stand 1 hour at room temperature, then brine is added and the organic layer separated, dried on sodium sulfate and evaporated to give an oily residue which is purified by flash chromatography (eluant: cyclohexane/ethyl acetate 4/1) to give (4) as a white solid (7.5 g; 47%; m.p. 87°–90° C.

EXAMPLE 2 a) (S)-2-[4-(N-t-butyloxycarbonyl-N-(3-fluorobenzyl)-aminobenzyl)]aminopropanamide (S)-(+) 2-aminopropanamide hydrochloride (2.7 g; 0.0217 mol) is dissolved in methanol (70 ml) under nitrogen, while stirring; to this solution, 2.7 g of 4 Å molecular sieves are added. The suspension formed is treated with sodium cyanoborohydride (1 g; 0.0157 mol) in a single portion at room temperature. To this mixture, 6.5 g (0.0197 mol) of 4-[N-t-butyloxycarbonyl-N-(3-fluorobenzyl)]amino-benzaldehyde (4) are added and the reaction kept 3 hours at room temperature. After filtration and evaporation, the crude oil obtained is purified by flash chromatography (eluant: dichloromethane/methanol/30% NH$_4$OH 190/10/1 to give (S)-2-[4-(N-t-butyloxycarbonyl-N-(3-fluoro-benzyl)aminobenzyl)]aminopropanamide as an oil (5 g; 64%).

b) (S)-2-[4-(3-fluorobenzyl)aminobenzyl]aminopropanamide dihydrochloride [FCE 27232A]

5 g (0.0124 mol) of 2-[4-(N-t-butyloxycarbonyl-N-(3-fluorobenzyl)aminobenzyl)]aminopropanamide are dissolved in 3.5 N HCl in ethanol and the mixture stirred at room temperature for 3.5 hours. After completion of the deprotection, the solution is evaporated, taken up with abs. ethanol, evaporated. The solid residue is triturated in ethyl ether, filtered, washed with ether and dried at 50° C./3 torr for 3 hours. 3.1 g (67%) of white plates of the title compound are obtained (m.p. 170° C. dec.), $[\alpha]_D^{25}+3.1$ (C=1.2 DMF).

Analogously, starting from (4) and (R)-(—)-2-aminopropanamide, the R-enantiomer can be obtained (m.p. 170° C. dec.), $[\alpha]_D^{25}-3.0$ (C=1.1 DMF).

Analogously, the following compounds can be obtained, either in R or S-enantiomeric form, starting from the corresponding aldehyde and the appropriate α-aminoamide.

2-[4-(2-fluorobenzyl)aminobenzyl]aminopropanamide, dihydrochloride, m.p. 135° C. (dec.);
2-[4-(2-chlorobenzyl)aminobenzyl]aminopropanamide, dihydrochloride;
2-[4-(3-chlorobenzyl)aminobenzyl]aminopropanamide, dihydrochloride, m.p. 180° C. (dec.);
2-[4-(2-bromobenzyl)aminobenzyl]aminopropanamide, dihydrochloride;
2-[4-(3-bromobenzyl)aminobenzyl]aminopropanamide, dihydrochloride, m.p. 180° C. (dec.);
2-[4-(4-fluorobenzyl)aminobenzyl]aminopropanamide, dihydrochloride, m.p. 195° C. (dec.);
2-[4-(4-bromobenzyl)aminobenzyl]aminopropanamide, dihydrochloride, m.p. 170° C. (dec.);
2-[4-(4-chlorobenzyl)aminobenzyl]aminopropanamide, dihydrochloride, m.p. 150° C. (dec.);
2- 4-[2-(2-fluorophenyl)ethyl]aminobenzyl aminopropanamide, dihydrochloride;
2- 4-[2-(3-fluorophenyl)ethyl]aminobenzyl aminopropanamide, dihydrochloride;
2- 4-[3-(2-fluorophenyl)propyl]aminobenzyl aminopropanamide, dihydrochloride;
2- 4-[3-(3-fluorophenyl)propyl]aminobenzyl aminopropanamide, dihydrochloride;
2-[4-(2-phenylethyl)aminobenzyl]aminopropanamide, dihydrochloride, m.p. 145° C. (dec.);
2-[4-(3-phenylpropyl)aminobenzyl]aminopropanamide, dihydrochloride;
2-[4-(4-phenylbutyl)aminobenzyl]aminopropanamide, dihydrochloride;
2- 4-[4-(2-fluorophenyl)butyl]aminobenzyl aminopropanamide, dihydrochloride;
2-4-[4-(3-fluorophenyl)butyl]aminobenzyl aminopropanamide, dihydrochloride;
2-[4-(2-methoxybenxyl)aminobenzyl]aminopropanamide, dihydrochloride;
2-[4-(3-methoxybenzyl)aminobenzyl]aminopropanamide, dihydrochloride;
2-[4-(2-trifluoromethylbenzyl)aminobenzyl]aminopropanamide, dihydrochloride; and
2-[4-(3-trifluoromethylbenzyl)aminobenzyl]aminopropanamide, dihydrochloride.

EXAMPLE 3

Tablets, each weighing 300 mg and containing 100 mg of the active substance can be manufactured as follows:

COMPOSITIONS (FOR 500 TABLETS)

| | |
|---|---|
| 2-[4-(3-fluorobenzyl)aminobenzyl]aminopropanamide, dihydrochloride | 500 g |
| Lactose | 710 g |
| Corn starch | 237.5 g |
| Talc powder | 37.5 g |
| Magnesium stearate | 15 g |

2-[4-(3-fluorobenzyl)amtnobenzyl]aminopropanamide, dihydrochloride, methanesulfonate, lactose and half of the corn starch are mixed; the mixture is then forced through a sieve of 0.5 mm openings. Corn starch (18 g) is suspended in warm water (180 ml).

The resulting paste is used to granulate the powder. The granules are dried, comminuted on a sieve size 1.4 mm, then the remaining quantity of starch, talc and magnesium is added, carefully mixed, and processed into tablets.

We claim:

1. A compound of formula (I)

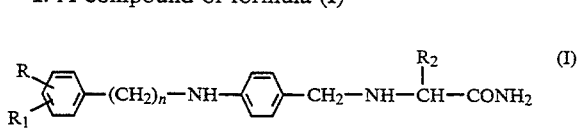

wherein n is an integer of 1 to 4; each of R and R₁, which may be the same or different, is hydrogen, halogen, trifluoromethyl or $C_1$-$C_4$ alkoxy; $R_2$ is hydrogen or $C_1$-$C_4$ alkyl; or a pharmaceutically acceptable salt thereof; and wherein when, at the same time, R and R₁ are both hydrogen, or when R or R₁ is hydrogen and the other is halogen and n is one, then R₂ is other than hydrogen or methyl.

2. A compound of formula (I), according to claim 1, wherein n is 1, 2, 3 or 4;
R is hydrogen; R₁ is hydrogen, halogen, $C_1$-$C_4$ alkoxy or trifluoromethyl; end
R₂ is $C_1$-$C_4$ alkyl; or a pharmaceutically acceptable salt thereof.

3. A compound which Is
2-[4-(2-methoxybenzyl)aminobenzyl]aminopropanamide;
2-[4-(3-methoxybenzyl)aminobenzyl]aminopropanamide;
2-[4-(2-trifluoromethylbenzyl)aminobenzyl]aminopropanamide;
2-[4-(3-trifluoromethylbenzyl)aminobenzyl]aminopropanamide;
2-{4-[2-(2-fluorophenyl)ethyl]aminobenzyl}aminopropanamide;
2-{4-[2-(3-fluorophenyl)ethyl]aminobenzyl}aminopropanamide;
2-{4-[3-(2-fluorophenyl)propyl]aminobenzyl}aminopropanamide;
2-{4-[3-(3-fluorophenyl)propyl]aminobenzyl}aminopropanamide;
2-{4-[4-( 3-fluorophenyl)butyl]aminobenzyl}aminopropanamide;
2-[4-(3-phenylpropyl)aminobenzyl]aminopropanamide;
2-[4-(2-phenylethyl)aminobenzyl]aminopropanamide;
2-{4-[4-(2-fluorophenyl)butyl]aminobenzyl aminopropanamide;
2-[4-(4-phenylbutyl)aminobenzyl]aminopropanamide; if the case, either as single (S) or (R) isomer or as a mixture thereof or a pharmaceutically acceptable salt thereof.

4. A compound of formula (IA)

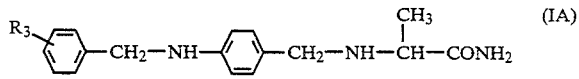

wherein R₃ is halogen,or a pharmaceutically acceptable salt thereof.

5. A compound which

2-[4-(4-fluorobenzyl)aminobenzyl]aminopropanamide;

2-[4-(4-chlorobenzyl)aminobenzyl]aminopropanamide;

2-[4-(4-bromobenzyl)aminobenzyl]aminopropanamide;

2-[4-(3-fluorobenzyl)aminobenzyl]aminopropanamide;

2-[4-(3-chlorobenzyl)aminobenzyl]aminopropanamide;

2-[4-(2-bromobenzyl)aminobenzyl]aminopropanamide;

2-[4-(2-chlorobenzyl)aminobenzyl]aminopropanamide;

2-[4-(2-fluorobenzyl)aminobenzyl]aminopropanamide;

2-[4-(3-bromobenzyl)aminobenzyl]aminopropanamide; if the case, as single (S) or (R) isomer or as a mixture thereof or a pharmaceutically acceptable salt thereof.

6. A pharmaceutical composition comprising a pharmaceutically acceptable carrier/and or diluent and, as an active principle, a compound of formula (I) or (IA), as defined in claim 1 or 4, or a pharmaceutically acceptable salt thereof.

7. A method of treating a patient suffering from epilespsy, comprising administering to the patient a therapeutically effective amount of a compound of formula (I) or (IA) as defined in claim 1 or 4, or a pharmaceutically acceptable salt thereof.

* * * * *